United States Patent [19]

Priegnitz et al.

[11] Patent Number: 5,645,729
[45] Date of Patent: *Jul. 8, 1997

[54] SEPARATIONS BY SIMULATED MOVING BED CHROMATOGRAPHY OPERATING AT LOW K' VALUES USING WEAKLY INTERACTING ADSORBENTS AS THE STATIONARY PHASE

[75] Inventors: James W. Priegnitz, Elgin; Beth Mc Culloch, Clarendon Hills, both of Ill.

[73] Assignee: UOP, Des Plaines, Ill.

[*] Notice: The term of this patent shall not extend beyond the expiration date of Pat. No. 5,518,625.

[21] Appl. No.: 572,911

[22] Filed: Dec. 15, 1995

Related U.S. Application Data

[63] Continuation-in-part of Ser. No. 387,984, Feb. 13, 1995, Pat. No. 5,518,625.

[51] Int. Cl.$^6$ .................................................... B01D 15/08
[52] U.S. Cl. .............................. 210/659; 210/198.2
[58] Field of Search .................................. 210/635, 656, 210/659, 198.2; 435/280

[56] References Cited

U.S. PATENT DOCUMENTS

| | | | |
|---|---|---|---|
| 5,126,055 | 6/1992 | Yamashita | 210/659 |
| 5,407,580 | 4/1995 | Hester | 210/635 |
| 5,433,793 | 7/1995 | Herber | 127/46.1 |
| 5,434,298 | 7/1995 | Negawa | 210/659 |
| 5,434,299 | 7/1995 | Negawa | 560/248 |

*Primary Examiner*—Ernest G. Therkorn
*Attorney, Agent, or Firm*—Thomas K. McBride; Eugene I. Snyder

[57] ABSTRACT

Resolution of a mixture of organic materials by simulated moving bed chromatography using a weakly interacting adsorbent as a stationary phase can be routinely effected with a liquid mobile phase characterized by atypically low values of k' with recoveries of at least 95% and a purity of at least 95%. In particular, values in the range $0.1 < k' < 1.0$ are recommended with a resulting savings in mobile phase consumption, inventory, and recovery.

3 Claims, 6 Drawing Sheets

SEPARATION FACTOR, $k'$

VOLUME-% METHANOL IN WATER

- $k'$ ETHYLPARABEN
- $k'$ PROPYLPARABEN

SEPARATIONS BY SIMULATED MOVING BED CHROMATOGRAPHY OPERATING AT LOW K' VALUES USING WEAKLY INTERACTING ADSORBENTS AS THE STATIONARY PHASE

CROSS REFERENCE TO RELATED APPLICATION

This application is a continuation-in-part of U.S. application Ser. No. 08/387,984, filed Feb. 13, 1995, now U.S. Pat. No. 5,518,625, all of which is incorporated by reference.

BACKGROUND OF THE INVENTION

This application deals with the use of chromatography in commercial scale preparative separations. More particularly, our invention deals with the branch of simulated moving bed chromatography as applied to separations where the stationary phase interacts only weakly with adsorbed materials. Our contribution to such separations which is the subject of this application arises from the recognition that operating at low values of k', the capacity factor, is quite beneficial in such separations even though classical liquid chromatography theory teaches operation at high values of k' as one prerequisite to successful separations. To better understand our invention in the context of theory and conventional practice it will be helpful to briefly review some of the relevant principles of liquid chromatography.

One fundamental property in liquid chromatography is k', the capacity factor, which is defined as $$k' = \frac{n_s}{n_m} \quad (1)$$

where $n_s$ is the total moles of material being separated in the stationary phase and $n_m$ is the number of moles in the mobile phase. Where there are several components present, the capacity factor for the ith component is $$k'(i) = \frac{n_s(i)}{n_m(i)}$$

The retention time, $t_r$, for component i, $t_r(i)$, is related to the time it takes for the mobile phase to travel the length of the column, $t_0$, by the distribution of component between the stationary and mobile phases according to the equation, $$t_r(i) = \frac{t_0}{\left[\frac{n_m(i)}{n_m(i) + n_s(i)}\right]} = t_0 \frac{[n_m(i) + n_s(i)]}{n_m(i)}$$

$$t_r(i) = t_0[1 + k'(i)]$$

Rearranging, $$k'(i) = \frac{t_r(i) - t_0(i)}{t_0(i)} \quad (2)$$

Thus, the capacity factor k' also is related to the relative retention time of the component in question.

For two components, the ratio of their relative retention times, α, is $$\alpha_{ij} = \frac{t_r(i) - t_0}{t_r(j) - t_0} = \frac{k'(i)}{k'(j)}$$

where $\alpha_{ij}$ is the selectivity factor between components i and j. Finally, the volume, $V_r$, of the mobile phase required to elute a component as measured to the apex of the peak is related to the flow rate, F, of the mobile phase and retention time of the component by, $$V_r(i) = t_r(i)F$$

from which it follows that $$V_r(i) = V_0[1 + k'(i)] \quad (4)$$

$$[V_r(i) - V_0]/V_0 = k' \quad (5)$$

and $$\frac{V_r(i) - V_0}{V_r(j) - V_0} = \frac{t_r(i) - t_0}{t_r(j) - t_0} = \frac{k'(i)}{k'(j)} = \alpha_{ij} \quad (6)$$

Thus, classical liquid chromatography theory as supported by much experimental evidence leads to the conclusions that the retention volume of a particular component, relative to the retention volume of the pure mobile phase, depends only on the capacity factor for the component, although relative retention volumes and relative retention times for two components depend only on the ratio of the two capacity factors, and it is the ratio of the capacity factors which define selectivity.

One form of chromatography well adapted to continuous, commercial-size separation is simulated moving bed chromatography. In continuous moving bed chromatography the stationary phase moves relative to the feed and mobile phase inputs, and the extract and raffinate outputs. Because of the difficulty in implementing a moving stationary phase in chromatographic separations its simulation is favored in practice (hence the name simulated moving bed chromatography) where incremental positional changes of the input and output streams, relative to a static stationary phase, is effected at regular intervals. Although many of the relations developed above apply to simulated moving bed chromatography some additional nuances are applicable when the separations are effected by weakly interacting adsorbents.

One important observation from the foregoing review of some salient theoretical aspects of liquid chromatography is the effect of k' on the retention time and retention volume, $$k' = t_r - t_0 = V_r - V_0$$

Whereas one normally seeks to maximize the difference in retention time between a component and the mobile phase in order to increase the difference in retention time between two components, this requires a large k' which has the ancillary undesirable effect of increasing the retention volume of the mobile phase for the components. Thus, the accepted practice in analytical chromatography and in batch mode preparative chromatography of operating at a high k', usually in the range 1<k'<10, has as a necessary consequence the usage of a large volume of mobile phase.

We have found the conditions in simulated moving bed chromatography can be significantly modified from those required for analytical and batch mode preparative chromatography. In particular, when weakly interacting adsorbents are used as the stationary phase, separations using simulated moving bed chromatography can be performed effectively at low values of k', thereby minimizing the amount of mobile phase which is needed. Specifically, such separations may be performed efficiently where k' is less than 1, and especially in the range 0.1<k'<1. Since an appreciable cost of the separation process is associated with the mobile phase and its recovery from the raffinate and extract streams, our process affords substantial cost savings accruing from a lower mobile phase inventory, lower utility costs in recovering the mobile phase, and other ancillary costs.

It needs to be mentioned that even though certain types of separation currently effected by simulated moving bed (SMB) processes operate at the equivalent of a low k' it is not obvious to extend this knowledge to separations using weakly interacting adsorbents as the stationary phase because the mechanism of adsorption is fundamentally different. Thus, the adsorbents used in traditional separations such as that of the xylene isomers are zeolites such as X faujasites that have a high ion exchange capacity. With zeolites, the primary mechanism for adsorption is electrostatic attraction. The heat of adsorption, which is a direct measure of strength of the bonding between the adsorbate and the surface, is high (typically ca. 20 kcal per mole). Consequently, a "strong" desorbent is required in these systems. Frequently, the desorbent is similar in polarity to that of the feed component. For example, xylenes are desorbed with alkyl aromatics such as p-diethylbenzene or toluene and cholorinated aromatic feedstocks are typical desorbed with chlorinated aromatic solvents. The strong adsorbate/adsorbent interaction and the high binding energies require the use of a strong desorbent.

The stationary phases which are the subject of this invention are weakly interacting adsorbents such as reverse phase materials, i.e., an organic moiety bonded to an underlying inert core support, usually silica, and more traditional adsorbents as carbon and ion-exchange resins. The mechanism of adsorption for the latter materials is very different from that of zeolites in that weak van der Waals forces predominate. Using reverse phase materials as an example, the adsorbate partitions between the "liquid phase" which is defined by the organic coating and molecules of the mobile phase. The binding energies between the weakly interacting adsorbent and the adsorbate often are less than 1 kcal per mole and the mobile phases are typically weak. Consequently, manipulation of the mobile phase composition and the use of "strong mobile phases" is unexpected for the very weak intermolecular interactions encountered with weakly interacting adsorbents as the stationary phase. We also shall see that solubility plays a more significant role in our invention than in prior SMB separations.

SUMMARY OF THE INVENTION

The purpose of this invention is to effect separations, especially of organic material, by simulated moving bed chromatography using as a stationary phase a weakly interacting adsorbent and using a conventional liquid mobile phase operating under separation conditions characterized by a low capacity factor for at least one of the separated materials. In an embodiment $0.1<k'<1.0$. In a more specific embodiment $0.3<k'<1.0$.

DESCRIPTION OF THE INVENTION

Figure 1:
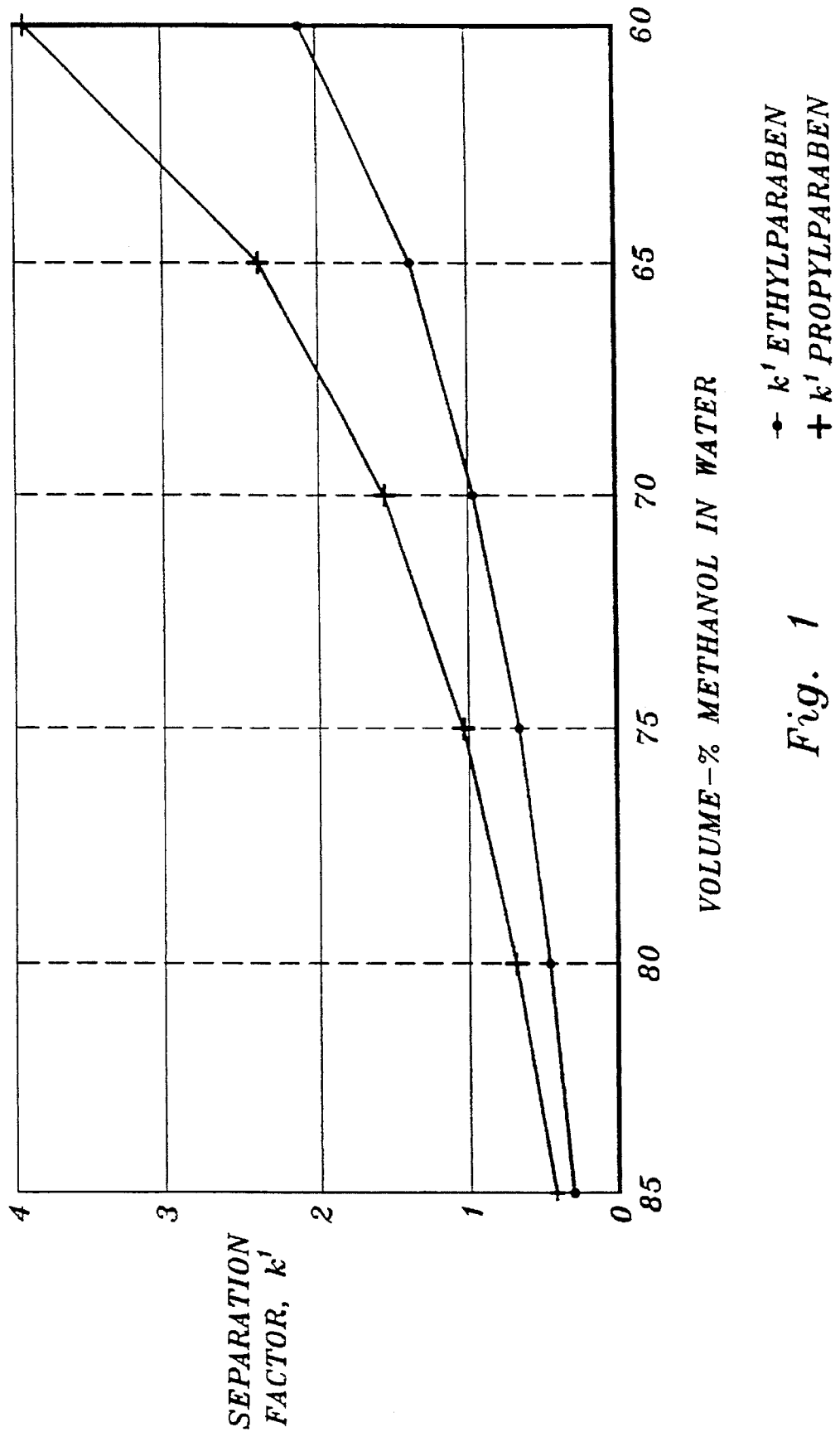
FIG. 1 depicts the effect of mobile phase composition on the separation factor.

Our invention results from the recognition that although a high value of retention capacity (i.e., capacity factor), k', is desirable and is usually posited as a necessary condition for the successful separation of two materials in traditional liquid chromatography, such a requirement is neither necessary nor desirable in effecting successful separations generally by simulated moving bed chromatography. Because the volume of the mobile phase used in eluting a material is proportional to k', a consequence of high k' values is a relatively large usage of the mobile phase. The larger the mobile phase usage, the higher the cost due to an increased solvent inventory, an increased cost of recovering the separated component from a larger volume of mobile phase, and higher inadvertent losses of mobile phase. Employing our invention leads to a substantial cost reduction and operating efficiency in effecting separations employing weakly interacting adsorbents as the stationary phase. In particular, our invention relates to the use of simulated moving bed chromatography for separations generally where one employs a conventional mobile phase and a solid stationary phase which interacts only weakly with the materials being adsorbed (adsorbates). The core of our invention is operating the SMB process under conditions where there is a low retention capacity for at least one of the materials separated, specifically $0.1<k'<1.0$ In traditional liquid chromatography $1.0<k'<10$. This condition has been used as both a desirable and necessary condition for adequate separation of components of interest. In simulated moving bed chromatography using a stationary phase which interacts only weakly with the adsorbates, we have found adequate separation can be achieved at $0.1<k'<1.0$. The benefits which flow need not be repeated; vide supra.

More particularly, the stationary phases to which our invention applies are adsorbents which interact only weakly with adsorbates. Such "weak interactions" are dominated by van der Waals forces with binding energies in the range from 1 kcal/mol up to about 4 kcal/mol. See Suzuki et al., AIChE Journal, March, 1995, p. 548. For example, the heat of adsorption of benzene on octadecylsilyl-silica is 1.6 kcal/mol. In the context of our invention "weakly interactive adsorbents" are those whose binding energy to the adsorbate of interest is not more than about 4 kcal per mole. Among the stationary phases of special interest are the various forms of carbon, ion-exchange resins, and the class generally referred to as "reverse phase" adsorbents. The latter may be characterized as a core support of a refractory inorganic oxide, generally silica, to which are bonded organic groups. See, e.g., "High Performance Liquid Chromatography. Analytical Chemistry by Open Learning," O. Kealy, Editor, J. Wiley and Sons, pp. 94–102; "Introduction to Modern Liquid Chromatography," L. R. Snyder and J. J. Kirkland, J. Wiley and Sons, pp. 270–288.

The following is a brief discussion on the types of stationary phases which we consider weakly interacting. Included are ion exchange, hydrophobic interaction and affinity chromatography which are widely used in the separations of proteins and peptides (bioseparations). Since one skilled in the art will be familiar with these stationary phases no detailed discussion or description is needed.

Normal phase chromatography is carried out with stationary phases which are relatively polar whereas reverse phase supports are relatively non-polar. Stationary phases used for normal phase applications are silica, alumina and bonded phases that contain amino, diamino, methylamino, cyano, diol and ether functional groups. Reverse phase stationary phases typically consist of alkyl or aromatic groups bonded to silica or other supports. The weakly interacting normal phase stationary phases (polar bonded phases) will be discussed under bonded phases. (Bonded phases can be used both under normal phase and reverse phase conditions.)

The most widely used bonded phases are based on siloxane (Si—O—Si—C) chemistry. Bonded phases are typically prepared by reaction of silica with organochlorosilane or organoalkoxysilane reagents to give a 'monomeric' bonded phase, i.e., one where the silicon of the silane has only a single (indirect) point of attachment to the silica (or other support) surface. An alternate route is to use di- or trichlorosilanes which give a cross linked polymeric layer at the silica surface, i.e., one where the silicon of the silane has multiple (indirect) points of attachment to the silica (or other support) surface.

Different bonded phases are prepared by varying the nature of the functional group R in the silylating agent. For example, the R group could be an alkyl with between 1 and 8 carbon atoms; $C_{18}$, $C_{20}$ or $C_{30}$ alkyl chain; an aromatic such as phenyl; or a functional group such as amino, diamino, methylamino, cyano, or diol and ether. Supports include silica and alumina and polymers such as methacrylate, styrene/DVB copolymer and polyvinyl alcohol. Other methods to prepare bonded phases include esterification of the surface silanol groups with alcohols, or conversion of the silanol groups to Si—Cl using thionyl chloride followed by reaction with an organometallic compound to give Si—C bonds or with an amine to give Si—N bonds.

A variety of other stationary phases show performance similar to the non-polar bonded phases. Examples are neutral polymeric resins, such as hydroxyethyl methacrylate and styrene/DVB copolymer, which interact by van der Waals forces. Graphitized and non graphitized carbon black and carbon-coated silica and zirconia coated with cross-linked polybutadiene also fall into this category.

Ion-exchange chromatography depends on the interaction between charged molecules in the stationary phase and charged solutes and ions in the mobile phase. Compounds can also be separated on the basis of ligand interaction with polar functional groups and a metal ion affixed to cationic sites of the packing. A wide variety of ion exchange packings are available. Hydrophobic ion exchangers are prepared from polymers such as polymethyl-methacrylate or polystyrene-divinylbenzene which are derivatized with sulfonic, carboxylic, quaternary and ternary ammonium groups. Ion exchanges based on silica, bonded with an organosilane, have also been prepared. Hydrophilic ion exchangers are prepared from polysaccharides and are derivatized with sulfonic, carboxylic, carboxymethyl (COO—), sulfopropyl (SO3—) diethylaminoethyl (DEAE), dimethylaminoethyl (DMAE), trimethylaminoethyl (TMAE), polyethyleneimine and trialkylammonium groups. Included in this class are beaded cellulose (Sephacel®), cross-linked dextran (Sephadex®) and cross-linked agarose (Sepharose®) the tentacle ion exchangers (Fractogel EMD®, see E. Merck Catalog pp. 67 and 71). Hydroxyapatite (calcium phosphate) has $Ca^{2+}$ and $PO_4^{3-}$ functional groups and is similar to a mixed mode ion exchange support in that it binds both acidic and basic proteins.

Hydrophobic Interaction Chromatography (HIC) separates proteins on the basis of relative hydrophobicity where the hydrophobic portion of the protein interacts with the hydrophobic surface of the packing. The mobile phase is an aqueous salt solution and proteins are eluted as the ionic strength decreases. Polymers such as polysaccharides, methacrylate copolymers and polystyrene-divinylbenzene are typically used. Commonly used hydrophobic ligands are phenyl, butyl and octyl groups. Examples of HIC media are the tentacle derivatives (Fractogel EMD®) and agarose derivatives (Sepharose®).

In affinity chromatograph, the molecule to be purified, is specifically and reversibly adsorbed by a complementary binding substance or ligand that is covalently attached to the stationary phase. Agarose is widely used as a support (Sepharose®) since the hydroxyl groups are can be easily derivatized for covalent attachment of ligands. Ligands such as heparin, protein A and Cibacron Blue have been used. Silica coated with a hydrophilic layer (glycophase) is also used as a support.

With bonded phases the intermolecular forces responsible for adsorption are primary van der Waals forces whereas with zeolites electrostatic interactions predominate. Typical heats of adsorption on bonded phases range from 1 to 4 kcal/mol (Suzuki et al, AIChE Journal March 1995, p 548). For example, the heat of adsorption of benzene on octadecylsilyl-silica is 1.6 kcal/mol. With a zeolite such as NaX, the corresponding heat of adsorption for benzene is 18 kcal/mole (Ruthven, 'Principles of Adsorption and Adsorption Processes' John Wiley & Sons, 1984, p 41).

EXAMPLES

The methodology used to identify the conditions for simulated moving bed (SMB) operation is discussed and exemplified. The optimal conditions can be readily identified by analyzing elution profiles obtained from HPLC (high performance liquid chromatography). Important parameters for optimization are loadability of the support, selectivity, mobile phase strength, and feed solubility. Optimization of these parameters helps identify conditions suitable for a cost-effective separation.

The experimental approach is outlined below. Although we believe our general approach is effective and efficient, we do not mean to imply that other alternatives are unavailable. We make our choice based on convenience, efficacy, and experience.

1. Identify a suitable stationary phase.
2. Determine the solubility properties of the feed material.
3. Identify a mobile phase that gives the best combination of selectivity and solubility.
4. Evaluate the effect of different mobile phase compositions.
5. Select the optimal mobile phase composition subject to the parameters of feed solubility, selectivity, and mobile phase strength.

The following case study is presented to demonstrate how our experimental approach is applied and illustrates how the selectivity varies with mobile phase composition. In each example productivity and mobile phase consumption are calcuhted from elution profile data for various mobile phase compositions. Optimal SMB conditions are derived from the productivity and mobile phase consumption data.

Definitions

Productivity refers to the mount of product (in grams) processed per liter of stationary phase per hour.
Mobile phase consumption refers to the amount of solvent required to process one gram of feed.
Target performance in the SMB operation is 99% purity of the extracted component and 99% recovery, where recovery refers to the yield of the extracted component.

An example of the effect of mobile phase composition is shown for a reverse phase $C_{18}$ stationary phase.

Separation of Ethyl and Propyl Parabens.

The separation of ethyl-paraben (ethyl 4-hydroxybenzoate) from propyl-paraben was investigated on a $C_{18}$ phase prepared by Knauer. The silica had a particle size distribution of 15 to 25 μm and was packed in a column with the dimensions of 0.8 cm ID by 25 cm length. The effect of a range of methanol/water mobile phase compositions on the separation performance in an SMB operation was evaluated. Typical experimental conditions involved the use of a feed stock consisting of 0.1 weight percent each of ethyl paraben and propyl paraben and 0.02 weight percent uracil (tracer) prepared in 60/40 volume percent methanol/water. A 5 μL injection volume was used and the flow rate was 3 mL/min. The detection wavelength was 254 nm.

SMB Performance.

Figure 2:
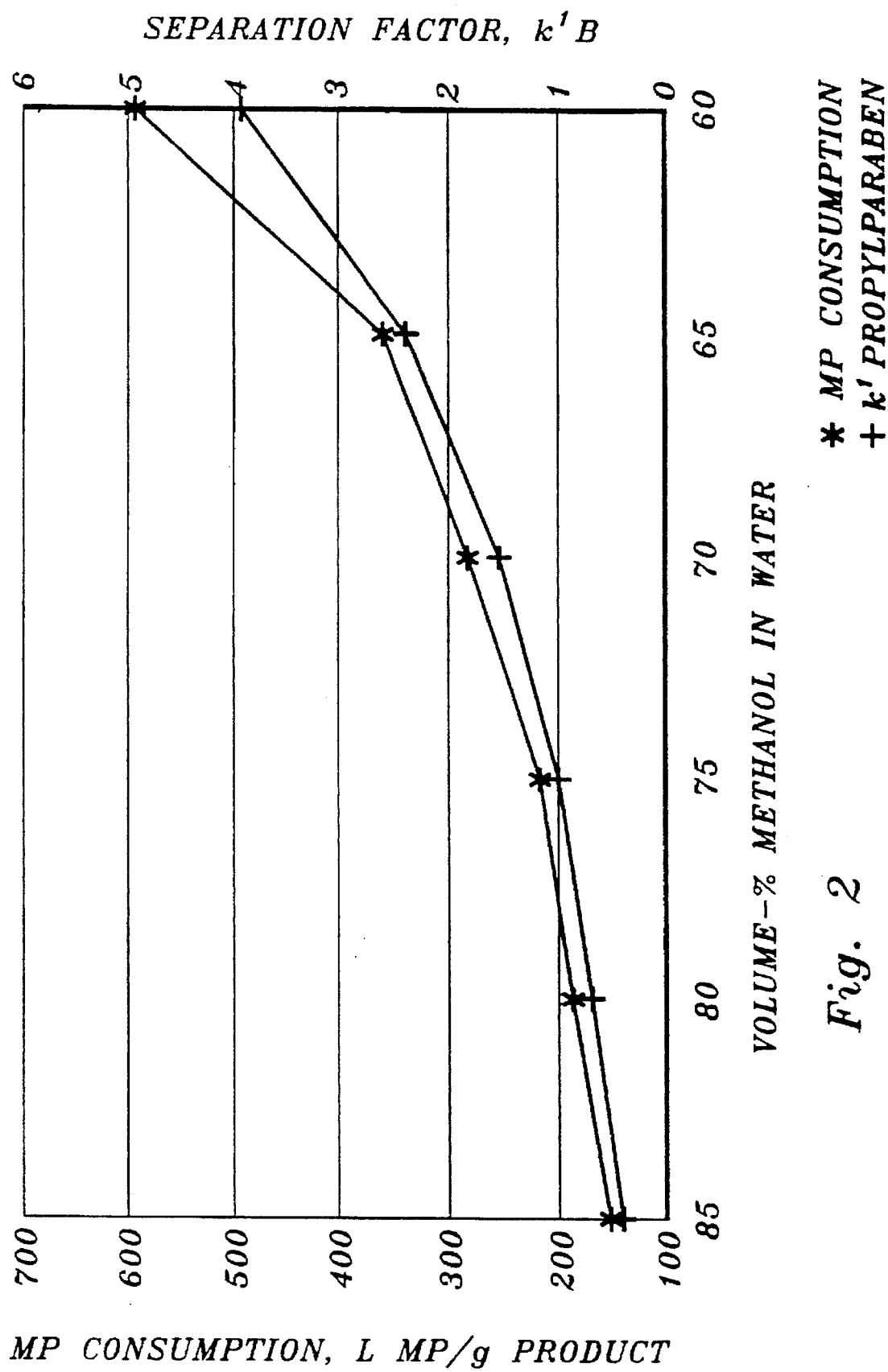
FIG. 2 depicts the change in mobile phase consumption versus the separation factor.

SMB performance was determined for 99.5% purity propyl paraben (extracted component) at 99% recovery. The productivity and mobile phase consumption were calculated from the elution profile data. The elution profile data are summarized in Table 1 and shown graphically in FIG. 1. The capacity factors, k's, increase as the methanol content of the mobile phase decreases. In an SMB operation, the mobile phase consumption increases from 153 liters of mobile phase per kilogram of product to 596 liters of mobile phase per kilogram of product over the range of mobile phase compositions investigated. The almost four-fold increase in mobile phase consumption correlates closely with the capacity factor, as shown in FIG. 2. In a commercial operation, the preferred mobile phase composition would be 75/25 volume percent methanol/water where the capacity factors are close to 1.

Figure 3:
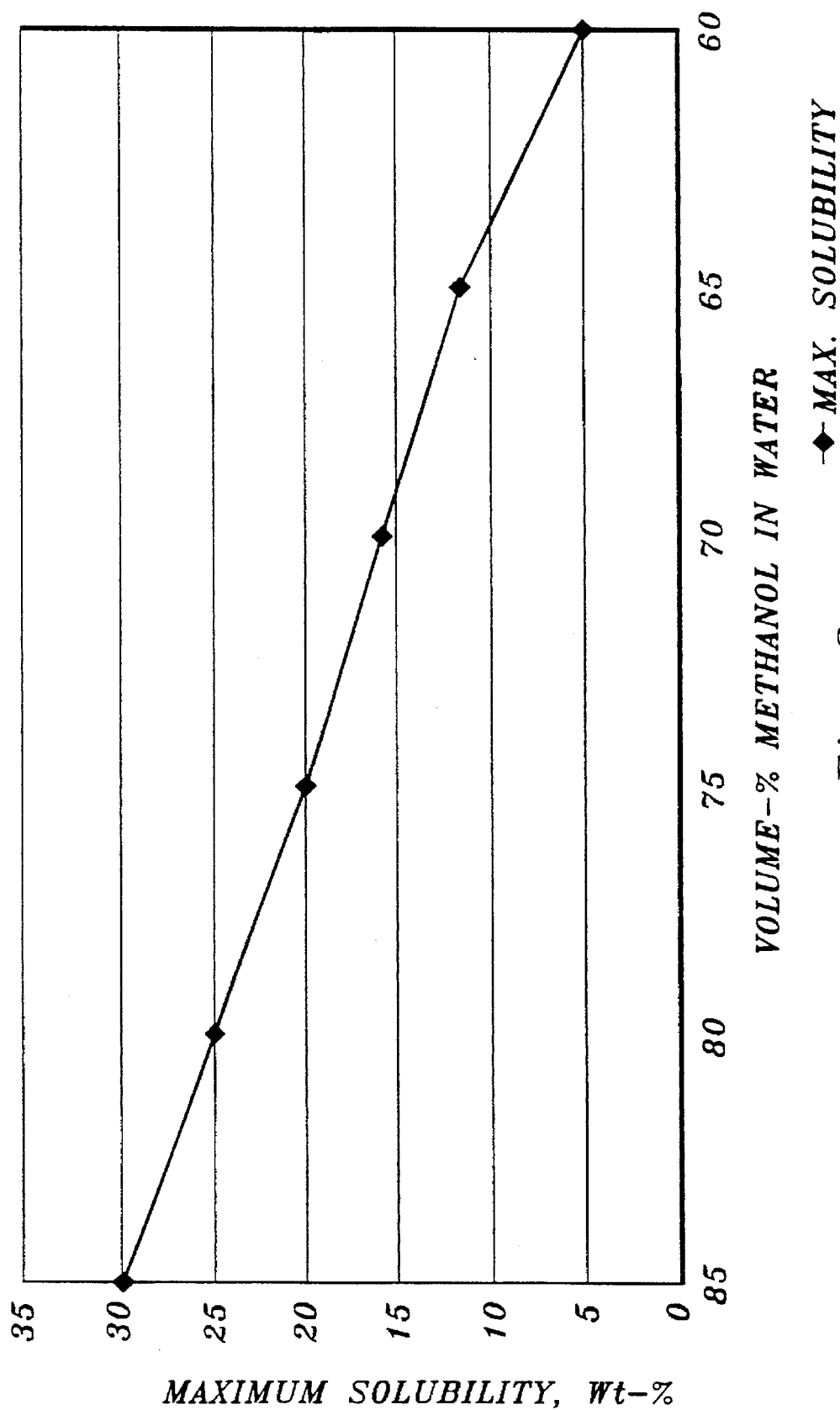
FIG. 3 depicts the maximum feed solubility with mobile phase composition change

An additional benefit of the high methanol content of the mobile phase is that good solubility of parabens is achieved (see FIG. 3). In 75/25 volume percent methanol/water, the solubility is 20 weight percent.

Figure 4:
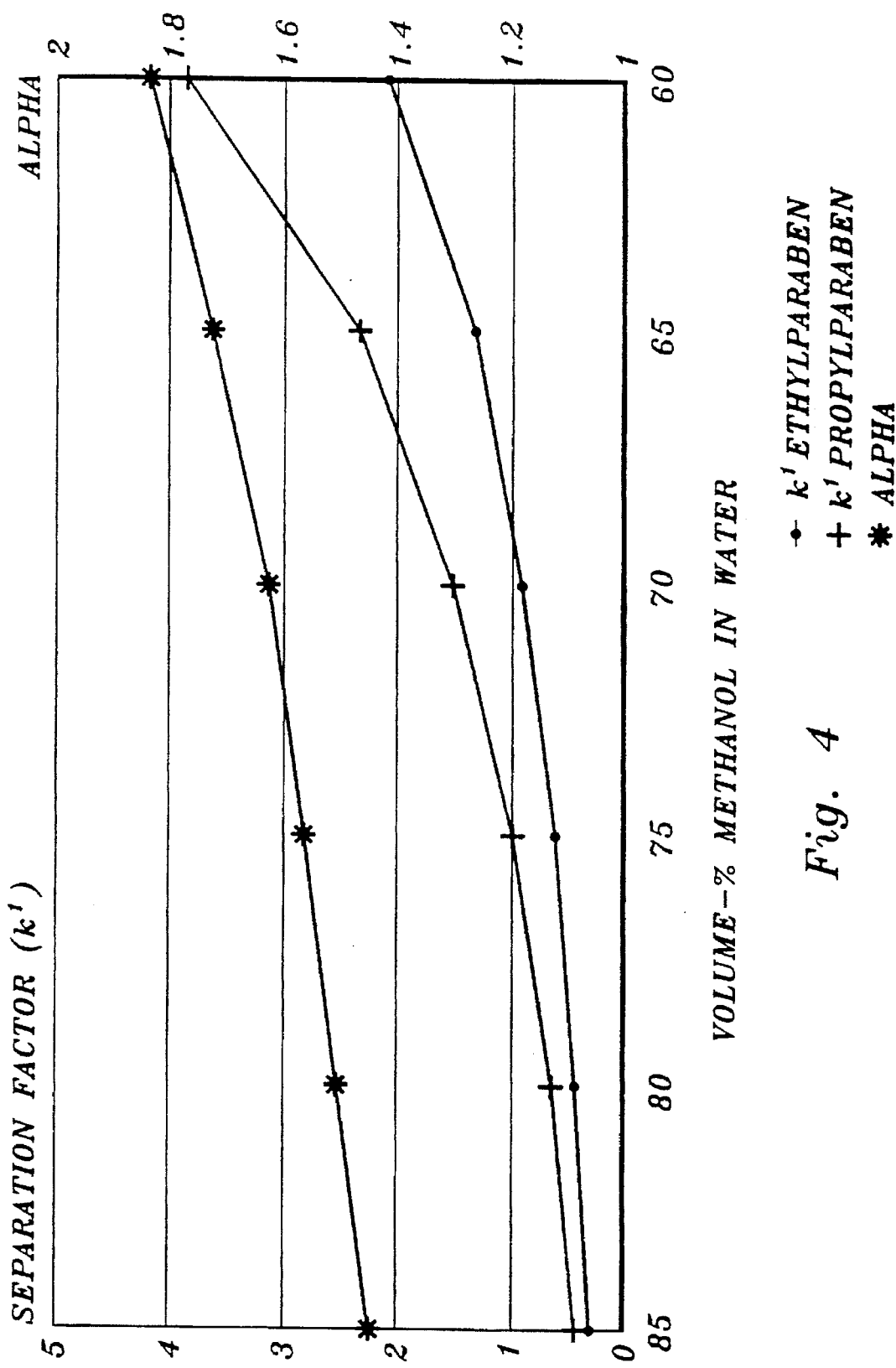
FIG. 4 depicts the change in selectivity versus separation factor.
Figure 5:
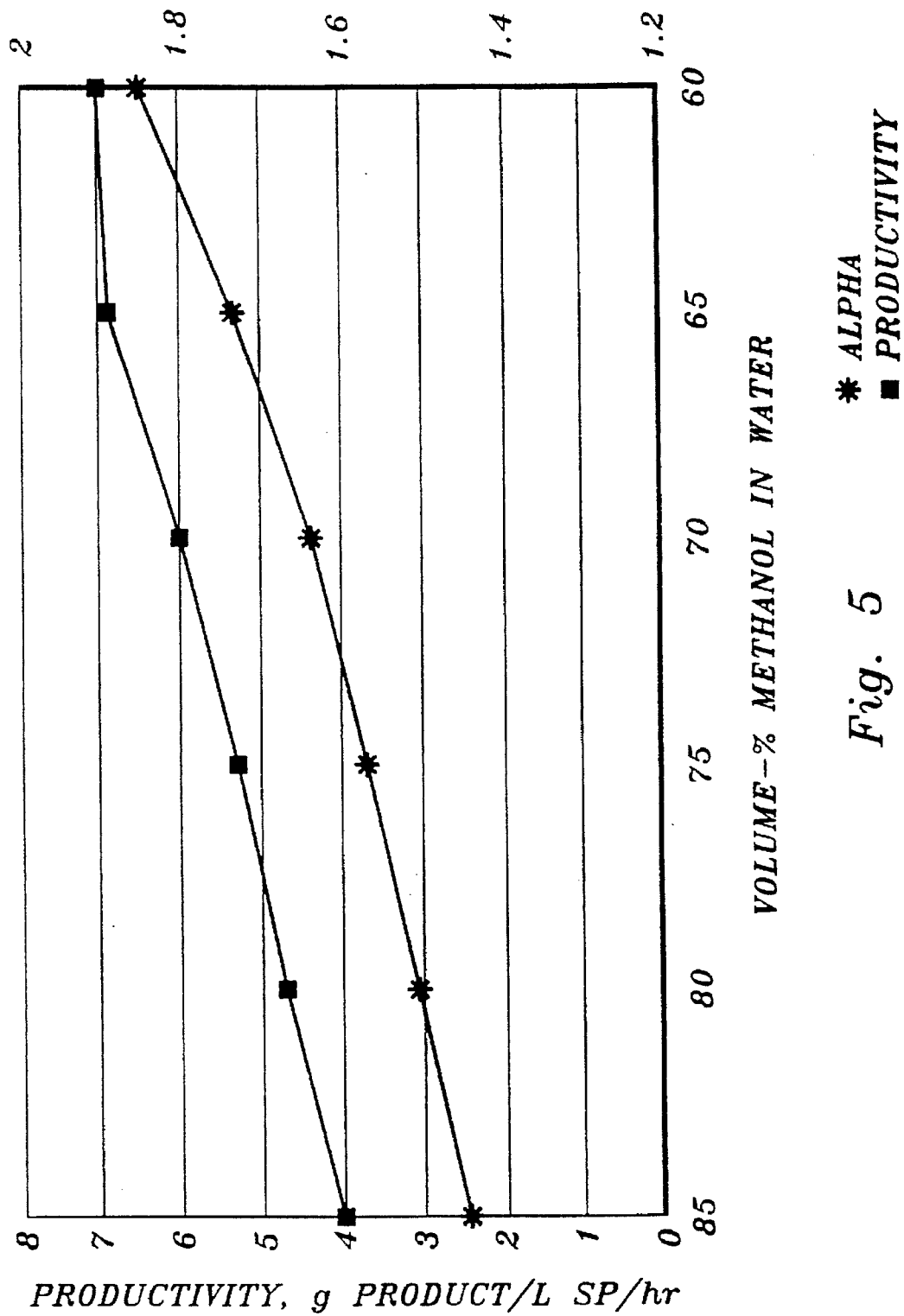
FIG. 5 depicts productivity versus selectivity.

With the separation of ethyl and propyl parabens on a $C_{18}$ phase, the selectivity is influenced by the mobile phase composition. FIG. 4 indicates that the selectivity increases from 1.45 to 1.85 over the range of mobile phase compositions investigated. The increase in selectivity is beneficial as the productivity, defined as grams product per liter stationary phase per hour, increases from 4 to 7. A correlation between the productivity and selectivity is shown in FIG. 5.

Figure 6:
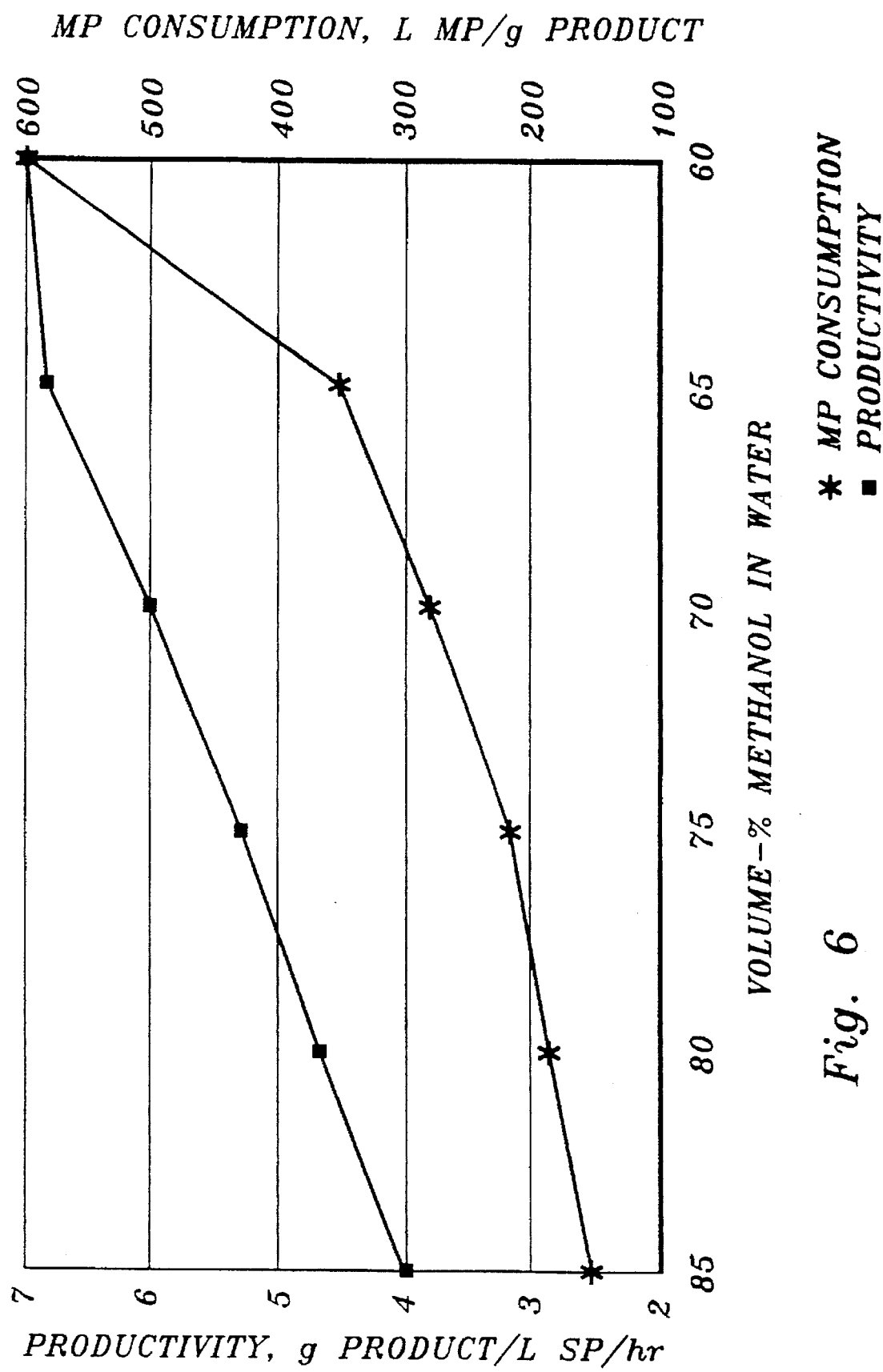
FIG. 6 depicts productivity versus mobile phase consumption.

Selection of the optimum operating conditions for SMB operation is based on economic factors. A high productivity would be attractive if the cost of the stationary phase were high as in the case of chiral stationary phases. With reverse phase or bare silica, where the cost of the stationary phase is low, solvent recovery costs dominate. Consequently, preferred operating conditions would be with a mobile phase composition of 75/25 volume percent methanol/water, see FIG. 6.

TABLE 1

| MP Composition Methanol/Water Volume Percent | k' | k' | ∞ | Sol weight percent | Prod. | MP Cons. |
|---|---|---|---|---|---|---|
| 85/15 | 0.29 | 0.42 | 1.45 | 30 | 4.0 | 153 |
| 80/20 | 0.46 | 0.69 | 1.51 | 25 | 4.7 | 187 |
| 75/25 | 0.65 | 1.03 | 1.57 | 20 | 5.3 | 218 |
| 70/30 | 0.96 | 1.56 | 1.64 | 16 | 6.0 | 285 |

TABLE 1-continued

| MP Composition Methanol/Water Volume Percent | k' | k' | ∞ | Sol weight percent | Prod. | MP Cons. |
|---|---|---|---|---|---|---|
| 65/35 | 1.38 | 2.42 | 1.74 | 12 | 6.9 | 359 |
| 60/40 | 2.13 | 3.94 | 1.85 | 5 | 7.0 | 596 |

Productivity is defined as grams Product/L Stationary Phase/hour.

MP Consumption is defined as L Mobile Phase/kilogram Product.

General Guidelines

The solubility of the feed material in the mobile phase is an important criterion for achieving a cost-effective separation using SMB technology. Productivity will be low if the feed has low solubility in the mobile phase of choice and the selectivity of the separation is low. Low productivity leads to high stationary phase requirements.

With high stationary phase costs, the savings in solvent recovery costs are less significant. A cost-effective SMB separation requires that the selectivity of the separation and the life of the stationary phase be maximized. With low stationary phase costs, the solvent recovery costs become significant. In most cases, it is desirable to operate with a mobile phase composition that gives capacity factors less than 1.

From the foregoing, distinctions between SMB and traditional elution chromatography, whether analytical or preparative batch chromatography, are apparent. In preparative chromatography, high resolution is required to obtain high purity and recovery. Resolution is proportional to k' and the use of low k's can result in low resolution. With SMB operation, however, good resolution (greater than 1) is not required. The countercurrent mode of operation is inherently more efficient and high purity and recovery can be achieved by "peak shaving." From the perspective of the elution chromatographer, the use of low values of k' in SMB operation is unexpected. Successful separations via SMB using weakly interacting adsorbents as the stationary phase can be routinely achieved working at a resolution less than 1, contrary to the current guidelines for elution chromatography. See, e.g., Kirkland and Snyder, page 52, who teach that the optimum k' range in elution chromatography is between 1 and 10.

Specifically, for eases where k'<1 the chromatographic resolution, Rs, is necessarily less than 0.5. But at these conditions for separation of a 1:1 mixture of 2 components the cutoff at the midpoint of the eluted peak affords 84% purity with about 84% recovery; see p. 34, FIG. 2.11 and page 48, FIG. 2.21, of Kirkland and Snyder, op. cit. However, working with SMB at an Rs of 0.5 one can readily obtain a purity of 95% at a recovery of 95%, which dramatically demonstrates the unexpected difference between elution chromatography and the SMB process. Separating materials with a purity of at least 98% and a recovery of at least 98% is a more preferred mode of operation and is generally readily achievable according to the practice of our invention.

What is claimed is:

1. In a process for the separation of at least one material from a mixture of organic materials by simulated moving bed chromatography using a weakly interacting adsorbent as a solid stationary phase, said stationary phase having a heat of adsorption for said organic materials of no more than about 4 kcal per mole, said stationary phase selected from the group consisting of reverse phase adsorbents, carbon, and ion-exchange resins, the improvement comprising effecting said separation using a liquid mobile phase which affords a retention capacity, k', such that $0.1 < k' < 1.0$.

2. The process of claim 1 where the separation affords at least one of the organic materials in at least 95% purity with at least 95% recovery.

3. The process of claim 1 where the separation affords at least one of the organic materials in at least 98% purity with at least 98% recovery.

* * * * *